(12) United States Patent
Inderberg et al.

(10) Patent No.: US 12,286,642 B2
(45) Date of Patent: Apr. 29, 2025

(54) CHIMERIC ANTIGEN RECEPTORS (CARS) THAT BIND OSTEOSARCOMA AND THEIR USE IN MEDICINE

(71) Applicant: Oslo Universitetssykehus HF, Oslo (NO)

(72) Inventors: Else Marit Inderberg, Oslo (NO); Sébastian Wälchli, Oslo (NO); Øyvind S. Bruland, Oslo (NO)

(73) Assignee: Oslo Universitetssykehus HF, Oslo (NO)

( * ) Notice: Subject to any disclaimer, the term of this patent is extended or adjusted under 35 U.S.C. 154(b) by 952 days.

(21) Appl. No.: 17/415,147

(22) PCT Filed: Dec. 19, 2019

(86) PCT No.: PCT/EP2019/086309
§ 371 (c)(1),
(2) Date: Jun. 17, 2021

(87) PCT Pub. No.: WO2020/127734
PCT Pub. Date: Jun. 25, 2020

(65) Prior Publication Data
US 2022/0175897 A1 Jun. 9, 2022

(30) Foreign Application Priority Data
Dec. 20, 2018 (NO) .................................. 20181636

(51) Int. Cl.
*C07K 19/00* (2006.01)
*A61K 39/00* (2006.01)
(Continued)

(52) U.S. Cl.
CPC ........ *C12N 5/0636* (2013.01); *A61K 39/4611* (2023.05); *A61K 39/4631* (2023.05);
(Continued)

(58) Field of Classification Search
None
See application file for complete search history.

(56) References Cited

U.S. PATENT DOCUMENTS 10,767,184 B2 * 9/2020 Kochenderfer ........ C07K 16/18
2019/0192573 A1 * 6/2019 Bjornsdorff .... A61K 39/464417

FOREIGN PATENT DOCUMENTS

WO 2016016341 A1 2/2016
WO 2017118745 A1 7/2017
(Continued)

OTHER PUBLICATIONS

Bruland et al., Expression and Characteristics of a Novel Human Osteosarcoma-associated Cell Surface Antigen, Canc. Res. 48: 5302-5309, Sep. 15, 1988.*
(Continued)

*Primary Examiner* — Claire Kaufman
(74) *Attorney, Agent, or Firm* — Karen A. LeCuyer; DeWitt LLP

(57) ABSTRACT

Chimeric antigen receptors (CARs) are provided. When the CARs herein are expressed on the surface of immune cells, such immune cells may be directed to osteosarcoma cells. In a murine intraperitoneal model, the tumor growth was significantly delayed for T cells expressing a CAR comprising a scFv from TP1 or TP3 antibodies. Immune cells expressing the CARs herein display therapeutic effect in the form of decreased tumor volume in a murine model simulating metastatic osteosarcoma. Combined with the finding that stem cells from healthy bone marrow were not significantly affected by T cells expressing any of the CARs, the CARs may be used for the treatment of osteosarcoma.

14 Claims, 10 Drawing Sheets
Specification includes a Sequence Listing.

(51) Int. Cl.
   A61P 35/04    (2006.01)
   C07K 14/705   (2006.01)
   C07K 16/30    (2006.01)
   C12N 5/0783   (2010.01)
   C12N 15/62    (2006.01)
(52) U.S. Cl.
   CPC .......... *A61K 39/4644* (2023.05); *A61P 35/04* (2018.01); *C07K 14/70517* (2013.01); *C07K 14/70532* (2013.01); *C07K 16/30* (2013.01); *C12N 15/62* (2013.01); *A61K 2039/86* (2018.08); *A61K 2239/31* (2023.05); *A61K 2239/55* (2023.05); *C07K 2317/622* (2013.01); *C07K 2317/73* (2013.01); *C07K 2319/03* (2013.01); *C07K 2319/33* (2013.01)

(56) References Cited

FOREIGN PATENT DOCUMENTS

| WO | WO 2017/217525 A1 | 12/2017 |
| WO | 2018033630 A1 | 2/2018 |
| WO | WO 2021/260129 A1 | 12/2021 |

OTHER PUBLICATIONS

GenBank Database, Accession No. AJ131748, version 1, Mus musculus mRNA for immunoglobulin heavy chain variable region, clone TP-1, Retrieved from <URL:https://www.ncbi.nlm.nih.gov/nuccore/AJ131748.1> [retrieved on May 15, 2024], Jul. 26, 2016.*
GenBank Database, Accession No. AJ131747, version 1, Mus musculus mRNA for immunoglobulin light chain variable region, clone TP-1, Retrieved from <URL:https://www.ncbi.nlm.nih.gov/nuccore/AJ131747.1> [retrieved on May 15, 2024], Jul. 26, 2016.*
Song et al. In vivo persistence, tumor localization, and antitumor activity of CAR-engineered T cells is enhanced by costimulatory signaling through CD137 (4-1BB). Cancer Res 2011;71:4617-4627 and supplementary materials.*
Wycislo et al., The Immunotherapy of Canine Osteosarcoma: A Historical and Systematic Review, J. Vet. Intern. Med. 2015;29:759-769.*
DeRenzo et al. (2014). Genetically Modified T-Cell Therapy for Osteosarcoma. In: Kleinerman, M.D., E. (eds) Current Advances in Osteosarcoma. Adv. Exp. Med. Biol. vol 804:323-340. Springer, Cham. https://doi.org/10.1007/978-3-319-04843-7_18. 22 pages.*
Li et al., Current status and future challenges of CAR-T cell therapy for osteosarcoma, Frontiers Immunol. 14:1290762, doi.org/10.3389/fimmu.2023.1290762, 12 pages, Dec. 22, 2023.*
Ahmed, N. et al.; "Human Epidermal Growth Factor Receptor 2 (HER2)—Specific Chimeric Antigen Receptor—Modified T Cells for the Immunotherapy of HER2-Positive Sarcoma"; Journal of Clinical Oncology, vol. 33, Issue No. 15; 2015; pp. 1688-1696.
International Search Report and Written Opinion for International Application PCT/EP2019/086309; International Filing Date: Dec. 19, 2019; Date of Mailing: May 11, 2020; 16 pages.
Köksal, H. et al.; "Chimeric antigen receptor preparation from hybridoma to T-cell expression"; Antibody Therapeutics, vol. 2, Issue No. 2; 2019; pp. 56-63.
Köksal, H. et al.; "Treating osteosarcoma with CAR T cells"; Scandinavian Journal of Immunology, vol. 89; 2018; 8 pages; doi: 10.1111/sji.12741.
Lauvrak, S. et al.; "Functional characterisation of osteosarcoma cell lines and identification of mRNAs and miRNAs associated with aggressive cancer phenotypes"; British Journal of Cancer, vol. 109, Issue No. 8; 2013; pp. 2228-2236.
Long, A. et al.; "Reduction of MDSCs with All-trans Retinoic Acid Improves CAR Therapy Efficacy for Sarcomas"; Cancer Immunology Research, vol. 4, Issue No. 10; 2016; pp. 869-880.
Morgan, R. et al.; "Case Report of a Serious Adverse Event Following the Administration of T Cells Transduced With a Chimeric Antigen Receptor Recognizing ERBB2"; Molecular Therapy, vol. 18, Issue No. 4; 2010; pp. 843-851.
Mount, C., et al.; "Potent antitumor efficacy of anti-GD2 CAR T cells in H3-K27M + diffuse midline gliomas"; Nature Medicine, vol. 24, Issue No. 5; 2018; pp. 572-579.
Olafsen, T. et al.; "Cloning and Sequencing of V Genes from Anti-Osteosarcoma Monoclonal Antibodies TP-1 and TP-3: Location of Lysine Residues and Implications for Radiolabeling"; Nuclear Medicine and Biology, vol. 22, Issue No. 6; 1995; pp. 765-771.
Olafsen, T.; "AJ131747: Mus musculus mRNA for immunoglobulin light chain variable region, clone TP-1"; Available on internet [https://www.ebi.ac.uk/ena/data/view/AL131747&display=text], retrieved Apr. 16, 2020; 2 pages.
Quintarelli, C. et al.; "Choice of costimulatory domains and of cytokines determines CAR T-cell activity in neuroblastoma"; Oncoimmunology, vol. 7, Issue No. 6; 2018; 16 pages; doi: 10.1080/2162402X.2018.1433518.
Srivastava, S., et al.; "Chimeric Antigen Receptor T Cell Therapy: Challenges to Bench-to-Bedside Efficacy"; Journal of Immunology, vol. 200, Issue No. 2; pp. 459-468.
Olafsen et al., "Erratum"; Nuclear Medicine and Biology, vol. 26; 1999; p. 599.
Wälchli, S. et al.; "A practical approach to T-cell receptor cloning and expression"; PLoS One, vol. 6, Issue No. 11; 2011; 11 pages; doi: 10.1371/journal.pone.0027930.
Walseng et al.; "A TCR-based Chimeric Antigen Receptor"; Scientific Reports, vol. 7, Issue No. 1; 2017; 10 pages; doi: 10.1038/s41598-017-11126-y.
Search Report received Oct. 30, 2023, for Chinese application No. 201980092529.1 with English Translation.

* cited by examiner mRNA

Retrovirus

CHIMERIC ANTIGEN RECEPTORS (CARS) THAT BIND OSTEOSARCOMA AND THEIR USE IN MEDICINE

CROSS REFERENCE TO RELATED APPLICATIONS

This application is a National Stage application of PCT/EP2019/086309, filed Dec. 19, 2019, which claims priority to Norwegian patent application No. 20181636, filed Dec. 20, 2018, both of which are incorporated by reference in their entirety herein.

SEQUENCE LISTING

The Instant Application contains a Sequence Listing which has been submitted electronically in ASCII format and is hereby incorporated by reference in its entirety. Said ASCII copy, created on Jan. 18, 2022 is named "OSA0063US Revised_ST25" and is 499 bytes in size.

TECHNICAL FIELD OF THE INVENTION

The invention is related to the field of cell therapy. In particular, it relates to chimeric antigen receptors (CARs), nucleic acids encoding CARs, immune cells expressing them and their utility in medicine for treatment of osteosarcoma.

BACKGROUND

Osteosarcoma (OS) is the most common primary bone cancer and the eighth most common form of cancer among children and adolescents. OS is an aggressive type of cancer with a 5-year overall survival as low as 60%. This number has not improved since the introduction of chemotherapy in the 70's. Although many international consortiums have been created to run clinical trials with innovative solutions, only poor results were reported so far. A reason for these negative results is related to the biology of OS. Most patients will succumb to their cancer due to lung metastasis, which are mostly chemoresistant. There is a clear unmet need in this area.

One clinical trial concerning sarcoma patients including osteosarcoma patients has been reported based on targeting of HER2 by autologous T cells expressing a CAR (Ahmed et al. 2015, J Clin Oncol. 2015 May 20; 33(15):1688-96). Although HER2 is present on various types of cancers, also healthy tissue expresses HER2. A patient receiving CAR T cells intravenously experienced respiratory distress within 15 minutes after cell infusion, and despite intensive medical intervention, the patient died 5 days after treatment (Morgan et al. Mol Ther. 2010 April; 18(4):843-51).

In order to achieve a therapeutic CAR T cell, the cell needs to express the CAR in a sufficient amount in the cell membrane and the antigen binding domain has to convey sufficient affinity and specificity in the CAR construct. Even subtle differences in the hinge may affect the ability of the CAR to reach the target epitope on a target cell and to subsequently deliver a signal into an immune cell.

Activity of CAR T cells in vitro may of course be an indication of in vivo activity. However, as disclosed by Long et al, Cancer Immunol Res. 2016 Oct.; 4(10): 869-880 in vitro activity of CAR T cells does not necessarily translate into in vivo efficacy, especially not for OS: "In vivo, however, GD2-CAR T cells mediated potent antitumor activity against neuroblastoma xenografts, but only minimal activity against osteosarcoma xenografts. The lack of antitumor activity was associated with sizable expansions of CD11b+Ly6G+ murine MDSCs that suppress human T cells". Furthermore, severe side effects may occur as disclosed by Mount et al, Nature Medicine volume 24, pages 572-579 (2018) where GD2-CAR T cell administration was tolerated in the majority of mice bearing orthotopic xenografts. Peritumoral neuroinflammation during the acute phase of antitumor activity resulted in hydrocephalus that was lethal in a fraction of animals.

In addition, CAR T cell therapy for solid tumors provides a different set of obstacles that needs to be overcome compared with hematologic malignancies. As described in Srivastava and Riddle, J Immunol 2018; 200:459-468; such obstacles include poor trafficking, enhanced expression of immunosuppressive molecules and cells, and immune checkpoints. For example, trafficking of CAR T cells to tumors is dependent upon expression of receptors for chemokines that are secreted by the tumor. Antigen-activated CAR T cells is further shown to upregulate expression of inhibitory receptors, which can lead to T cell dysfunction. Immunosuppressive molecules and cells can promote tumor growth and inhibit T cell activity both directly and indirectly. Accordingly, a variety of obstacles will need to be overcome for CAR T cells to be effective in solid tumors.

Another issue is related to efficient access of CAR T cells at the target site. In contrast to hematological malignancies, recognition of solid tumors requires egress from the blood into the tumor site, and many malignancies evolve such that T cell infiltration is actively impeded.

It can be expected that only a fraction of CAR T cells with in vitro activity will successfully migrate to tumor metastases in vivo and infiltrate the hostile tumor microenvironment of a solid tumor like OS. Furthermore, the CAR T cells will likely need to sustain their activity over time in order to provide a therapeutic effect in vivo. As disclosed by Quintarelli et al, ONCOIMMUNOLOGY 2018, VOL. 7, NO. 6, the signaling domains of the CAR constructs are of importance: "Nevertheless, when mCAR.GD2 T cells with the two different costimulatory signalling domains were tested in a xenograft NSG mouse model, we observed that only CARGD2.28.4-1BBz T cells mediated sustained antitumor effects in vivo (FIG. 2D-F). [ . . . ] Clinical trials conducted so far in children with NB using both 1st[7,18] and 3rd (CD28.OX40)[21] generation CARs targeting GD2 have demonstrated only limited efficacy."

It is therefore not trivial, but very desirable to obtain a novel CAR able to provide a therapeutic effect on OS in vivo when expressed in the cell membrane of immune cells.

SUMMARY

Novel chimeric antigen receptors (CARs) are provided. Immune cells expressing the CARs herein display therapeutic effect in murine models simulating metastatic OS, i.e. mice with OS tumors established in lungs, see FIGS. 7, 8 and 9. OS is a solid tumor, which often spreads to the lungs with fatal consequences. The CARs presented herein recognize a lung metastasis specific marker which was previously shown to be very specific. In addition, we assessed CAR safety by testing their reactivity against healthy tissues. Combined with the finding that stem cells from healthy bone marrow were not significantly affected by T cells expressing any of the CARs, this disclosure provides an attractive cell therapeutic alternative for treatment of OS in human patients.

Furthermore, immune cells expressing the CARs also demonstate activity in a model simulating micrometastic OS (see FIG. 10).

When the CARs herein are expressed on the surface of immune cells, such immune cells may be directed to OS cells as demonstrated with our in vivo data. A therapeutic effect in several xenograft OS models has been demonstrated. In a murine intraperitoneal model, the tumor growth was significantly delayed for T cells expressing a CAR comprising an antigen binding domain comprising SEQ ID NO 1 and SEQ ID NO 2 (TP1 scFv-fragment). In the same model, the tumor growth was essentially avoided for T cells expressing a CAR comprising an antigen binding domain comprising SEQ ID NO 3 and SEQ ID NO 4 (TP3 scFv-fragment). Furthermore, the overall survival was significantly improved for mice receiving T cells expressing either CAR. Intravenous administration of T cells expressing OSCAR1 or OSCAR3 provided a therapeutic effect and prolonged survival in mice with very aggressive OSA lung tumors and seemed to even prevent bone metastases (see FIGS. 7 and 8). Intravenous administration of T cells expressing OSCAR1 or OSCAR3 also provided an extended therapeutic effect in mice with LM-7 lung tumors (see FIG. 9).

In a first aspect, a CAR comprising an antigen binding domain, a hinge domain, a transmembrane domain and an intracellular signaling domain is provided; wherein the antigen binding domain comprises a TP1 scFv-fragment, or wherein the antigen binding domain comprises a TP3 scFv-fragment; the hinge domain comprises a CD8a hinge domain, the intracellular signaling domain comprises a CD3ζ signaling domain.

Said hinge domain may be represented by SEQ ID NO 5.

Said transmembrane domain may be represented by SEQ ID NO 6.

Said intracellular signaling domain may comprise a CD3ζ signaling domain and a. costimulatory domain.

Said intracellular signaling domain may comprise a CD3ζ signaling domain and a 4-1BB costimulatory domain.

Said intracellular signaling domain may consist of a CD3ζ signaling domain and a 4-1BB costimulatory domain.

Said antigen binding domain may comprise SEQ ID NO 1 and SEQ ID NO 2 connected by a peptide linker.

Said antigen binding domain may comprise SEQ ID NO 3 and SEQ ID NO 4 connected by a peptide linker.

Said antigen binding domain may comprise SEQ ID NO 1 and SEQ ID NO 2 connected by a peptide linker, the hinge domain may be represented by SEQ ID NO 5, the transmembrane domain may be represented by SEQ ID NO 6, and the intracellular signaling domain may comprise a CD3ζ signaling domain and a 4-1BB costimulatory domain.

Said antigen binding domain may comprise SEQ ID NO 3 and SEQ ID NO 4 connected by a peptide linker, the hinge domain may be a CD8a hinge domain represented by SEQ ID NO 5, the transmembrane domain may be a CD8a transmembrane domain represented by SEQ ID NO 6, and the intracellular signaling domain may comprise a CD3ζ signaling domain and a 4-1BB costimulatory domain.

In second aspect, a nucleic acid encoding the CARs according to the first aspect is provided.

In a third aspect, an immune cell transduced with the nucleic acid according to second aspect is provided.

In a fourth aspect, an immune cell expressing the CARs according to the first aspect is provided.

In a fifth aspect, a pharmaceutical composition comprising immune cells according the third or fourth aspect is provided.

Said pharmaceutical composition may be used in treatment of osteosarcoma

Said pharmaceutical composition may be used in treatment of metastatic osteosarcoma Said pharmaceutical composition may be used in treatment of micrometastatic osteosarcoma.

There is also proved an immune cell expressing a chimeric antigen receptor (CAR) in its cell membrane for use in treatment of metastatic osteosarcoma, wherein said CAR comprises an antigen-binding domain comprising a TP1 scFv-fragment or a TP3 scFv-fragment; a hinge domain, a transmembrane domain, an intracellular signaling domain, and optionally one or more costimulatory signaling domains.

There is also provided a method for treatment of osteosarcoma in a patient comprising the step of administering a pharmaceutically effective dose of a pharmaceutical composition according to the fifth aspect intravenously to the patient.

There is also provided a method for treatment of metastatic osteosarcoma in a patient comprising the step of administering a pharmaceutically effective dose of a pharmaceutical composition according to the fifth aspect intravenously to the patient.

DETAILED DESCRIPTION

Figure 1:
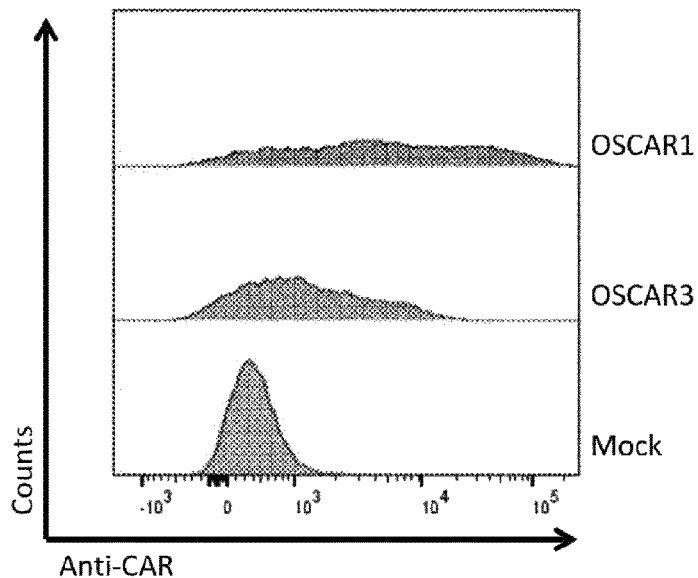
FIG. 1 shows that both CAR constructs (OSCAR1 and OSCAR3) are well expressed in primary T cells retrovirally transduced, and can be detected with an anti-mouse Fab antibody.
Figure 2:
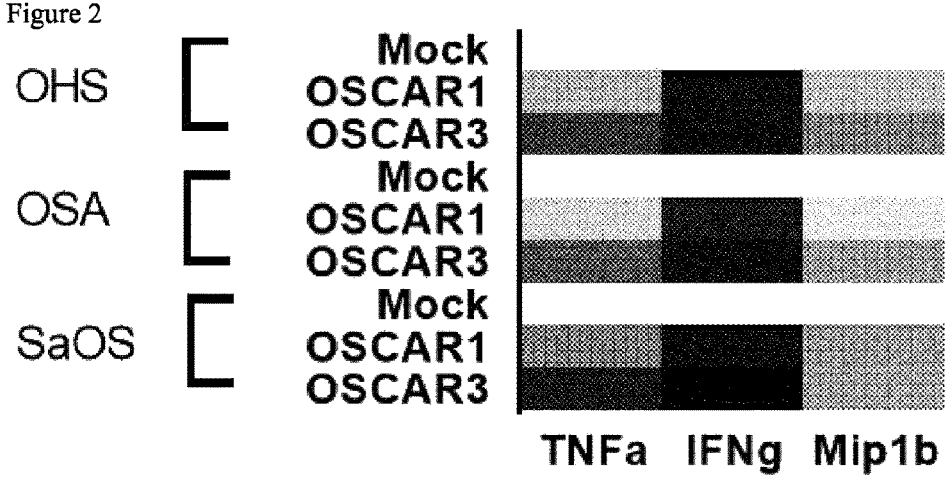
FIG. 2 shows cytokine release in cell medium detected by BioPlex. Darker color indicates higher cytokine level in the supernatant after 24 hours. As shown, the OSCAR redirected cells were strongly activated for TNFα and IFNγ release upon stimulation from osteosarcoma cell lines.

As used herein, Chimeric Antigen Receptors (CARs) are receptors comprising an extracellular antigen binding domain, a transmembrane domain and an intracellular signaling domain.

As used herein, an antigen binding domain is a protein moiety able to bind an extracellular target epitope under physiological conditions, in particular physiological conditions in a tumor environment. The antigen binding domain comprises two sequences; one variable domain from an antibody light chain (VL) and one variable domain from an antibody heavy chain (VH). Without being bound by theory, the target of the antigen binding domains herein may be p80. This antigen is believed to be a suitable target for OS therapy as it seems to be expressed by the cancer cells as well as budding capillaries associated with the tumor.

The VH and VL sequences may be connected by a disulphide bridges or a peptide linker. Alternatively, the two sequences may be embedded in a Fab-fragment of an antibody. In one embodiment, the antigen binding domain comprises or consists of VL-linker-VH. In another embodiment, the antigen binding domain comprises or consists of VH-linker-VL. Such antigen binding domains are often referred to as single chain Fv-fragments (scFv). The linker has to have a certain length in order to allow the VH and VL to form a functional antigen binding domain. In one embodiment, the linker comprises 10 to 30 amino acid residues. In one embodiment, the linker comprises 15 to 25 glycine and/or serine residues. In one embodiment, the linker is represented by the sequence GGGGSGGGGSGGGGSGGGGS (SEQ ID NO 9).

Each VL and VH comprises three complementarity determining regions (CDRs) flanked by framework sequences. It can be expected that the framework sequences may tolerate some variation without destroying the specificity and affinity to the target antigen. For example substitutions of amino acid residues may be tolerated better than deletions or additions of amino acid residues. However, the CDRs are generally more sensitive, but occasionally conservative substitutions may be introduced without destroying the specificity and affinity.

In one embodiment, the antigen binding domain comprises a TP1 scFv-fragment. The TP1 scFv-fragment comprises a TP1 VL and a TP1 VH connected by a peptide linker. In one embodiment, the antigen binding domain comprises SEQ ID NO 1 or sequences with more than 90% sequence identity to SEQ ID NO 1; and SEQ ID NO 2 or sequences with more than 90% sequence identity to SEQ ID NO 2.

In one embodiment, the antigen binding domain comprises SEQ ID NO 1 or sequences with more than 90% sequence identity to SEQ ID NO 1; and SEQ ID NO 2 or sequences with more than 90% sequence identity to SEQ ID NO 2; provided that any difference to said sequences is in the form of conservative substitution of amino acid residues.

In one embodiment, the antigen binding domain comprises SEQ ID NO 1 or sequences with more than 90% sequence identity to SEQ ID NO 1 provided the CDRs are unmodified; and SEQ ID NO 2 or sequences with more than 90% sequence identity to SEQ ID NO 2 provided the CDRs are unmodified.

In one embodiment, the antigen binding domain comprises SEQ ID NO 1 or sequences with more than 95% sequence identity to SEQ ID NO 1; and SEQ ID NO 2 or sequences with more than 95% sequence identity to SEQ ID NO 2; provided that any difference to said sequences is in the form of conservative substitution of amino acid residues.

In one embodiment, the antigen binding domain comprises a TP3 scFv-fragment. The TP3 scFv-fragment comprises a TP3 VL and a TP3 VH connected by a linker. In one embodiment, the antigen binding domain comprising SEQ ID NO 3 or sequences with more than 90% sequence identity to SEQ ID NO 3; and SEQ ID NO 4 or sequences with more than 90% sequence identity to SEQ ID NO 4.

In one embodiment, the antigen binding domain comprises SEQ ID NO 3 or sequences with more than 90% sequence identity to SEQ ID NO 3; and SEQ ID NO 4 or sequences with more than 90% sequence identity to SEQ ID NO 4; provided that any difference to said sequences is in the form of conservative substitution of amino acid residues.

In one embodiment, the antigen binding domain comprises SEQ ID NO 3 or sequences with more than 90% sequence identity to SEQ ID NO 3 provided the CDRs are unmodified; and SEQ ID NO 4 or sequences with more than 90% sequence identity to SEQ ID NO 4 provided the CDRs are unmodified.

In one embodiment, the antigen binding domain comprises SEQ ID NO 3 or sequences with more than 95% sequence identity to SEQ ID NO 3; and SEQ ID NO 4 or sequences with more than 95% sequence identity to SEQ ID NO 4; provided that any difference to said sequences is in the form of conservative substitution of amino acid residues.

The term "conservative amino acid substitution", as used herein, refers to an amino acid substitution in which one amino acid residue is replaced with another amino acid residue having a similar side chain. Amino acids with similar side chains tend to have similar properties, and thus a conservative substitution of an amino acid important for the structure or function of a polypeptide may be expected to affect polypeptide structure/function less than a non-conservative amino acid substitution at the same position. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine), non-polar side chains (e.g. glycine, cysteine, alanine, valine, leucine, isoleucine, proline, phenylalanine, methionine, tryptophan) and aromatic side chains (e.g. tyrosine, phenylalanine, tryptophan, histidine). Thus, a conservative amino acid substitution may be considered to be a substitution in which a particular amino acid residue is substituted for a different amino acid residue in the same family.

Novel chimeric antigen receptors (CARs) are provided. When the CARs herein are expressed on the surface of immune cells, such immune cells may be used in medicine. In particular, said immune cells may be used in treatment of osteosarcoma. In one embodiment, said immune cells be used in treatment of metastatic osteosarcoma.

CARs in the present disclosure may comprise any of the antigen binding domains as mentioned above. In particular, the CARs in the present disclosure may comprise any of the antigen binding domains as mentioned above connected to a CD8a hinge. In particular, the CARs in the present disclosure may comprise any of the antigen binding domains as mentioned above connected to a CD8a hinge, wherein the CAR further comprises a transmembrane domain and wherein the intracellular signaling domain comprises or consists of one costimulatory domain selected from 4-1BB and OX40 and a CD3ζ signaling domain.

In one particular embodiment, the CAR comprises an antigen-binding domain comprising a TP1 scFv-fragment or a TP3 scFv-fragment, a CD8a hinge domain connected to the antigen-binding domain, a transmembrane domain connected to the hinge domain and an intracellular signaling domain comprising a CD3ζ signaling domain and a 4-1BB costimulatory domain connected to the transmembrane domain.

Figure 11:
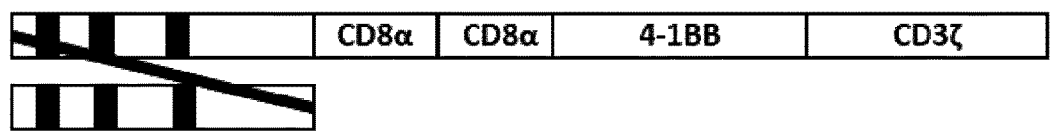
FIG. 11 visualizes the schematic structure of OSCAR1 and OSCAR3 from N-terminal to C-terminal. Both CARs comprise a scFv connected to CD8a hinge which in turn is connected to a CD8a transmembrane domain. The intracellular signaling domain comprises a 4-1BB costimulatory domain and a CD3ζ signaling domain.

The efficacy and safety of two CARs are demonstrated in the examples. One CAR, referred to as OSCAR1, consists of SEQ ID NO 1-SEQ ID NO 9-SEQ ID NO 2-SEQ ID NO 5-SEQ ID NO 6-SEQ ID NO 7-SEQ ID NO 8 from N-terminal to C-terminal. The other CAR, referred to as OSCAR3, consists of SEQ ID NO 3-SEQ ID NO 9-SEQ ID NO 4-SEQ ID NO 5-SEQ ID NO 6-SEQ ID NO 7-SEQ ID NO 8 from N-terminal to C-terminal. The schematic structure of OSCAR1 and OSCAR3 is visualized in FIG. 11.

The antigen-binding domain may be directly attached to a transmembrane domain. However, the CARs may comprise a hinge domain connecting the antigen binding domain to the transmembrane domain. The hinge domain may thus affect the sterically conformation of the antigen binding domain. This may in turn affect the ability of the CAR to bind the target epitope and subsequently trigger signaling into an immune cell. If the target epitope is located too far from the cell membrane of the target cell or if the target epitope is otherwise hidden, the immune cell expressing the CAR may not be efficient. Accordingly, it is preferred that the target epitope is sufficiently accessible for immune cells expressing the CARs. It is found that a CD8α hinge domain represented by SEQ ID NO 5 in the CARs disclosed herein allows the antigen binding domain to bind to the target epitope and allows activation of the immune cell expressing it. Other CD8a hinges may work as well provided they allow a similar sterical conformation of the antigen binding domain. In particular, such hinges may comprise approximately the same number of amino acid residues as the CD8a hinge represented by SEQ ID NO 5. In particular, the CD8α hinge can be represented by SEQ ID NO 5 or sequences with more than 90% sequence identity thereto. In one embodiment, the hinge domain is not from CD28.

As used herein, "X % sequence identity" means that X % of the amino acid residues are identical between two sequences when aligned and compared by BLAST® with the blastp algorithm.

The transmembrane domain connects the extracellular domains to an intracellular signaling domain. Both the antigen binding domain and hinge domain are extracellular domains, i.e. that they generally face the extracellular environment when expressed in the cell membrane of an immune cell. As used herein, "transmembrane domain", means the part of the CAR which tend to be embedded in the cell membrane when expressed by an immune effector cell. Suitable transmembrane domains are well known for skilled persons. In particular, transmembrane domains from CD8α, CD28 or ICOS may be used. In one embodiment, the transmembrane domain is not from CD28. The transmembrane domain is believed to convey a signal into immune cells upon binding of a target by the antigen binding domain. It is found that a CD8α transmembrane domain represented by SEQ ID NO 6 allows signaling into an immune cell upon binding of a target.

The "intracellular signaling domain" refers to a part of the CAR located inside the immune cell when the CAR is expressed in the cell membrane. These domains participate in conveying the signal upon binding of the target. A variety of signaling domains are known, and they can be combined and tailored to fit the endogenous signaling machinery in the immune cells.

In one embodiment the intracellular signaling domain comprises a "signal 1" domain like the signaling domains obtainable from CD3ζ, FcR-γ, CD3ε etc. In general, it is believed that "signal 1" domains (e.g. CD3ζ signaling domain represented by SEQ ID NO 8) convey a signal upon antigen binding.

In another embodiment, the intracellular signaling domain comprises a costimulatory domain. Such domains are well known and often referred to as "signal 2" domains, and they are believed to, subsequently of "signal 1" domains, convey a signal via costimulatory molecules. The "signal 2" is important for the maintenance of the signal and the survival of the cells. If absent, like in first generation CARs, the redirected cell may be efficient in killing and in early cytokines release, but will often become exhausted over time. Examples of such commonly used "signal 2" domains include 4-1BB signaling domain, CD28 signaling domain, 4-1BB signaling domain and ICOS signaling domain.

In particular, it is found that cytotoxic immune cells expressing the CARs herein provide an in vivo effect in OS models when the intracellular signaling domain comprises or consists of a CD3ζ signaling domain (SEQ ID NO 8) and a 4-1BB costimulatory domain (SEQ ID NO 7).

The immune cells expressing the CARs herein may be isolated from a patient or a compatible donor by leukapheresis or other suitable methods. Such primary cells may for example be T cells or NK cells. In particular, autologous T cells (both cytotoxic T cells, T helper cells or mixtures of these) may be transduced with nucleic acids encoding the CARs before a pharmaceutical composition comprising the cells is administered back to the patient. The immune cells expressing the CARs may also be cell lines suitable for clinical use like NK-92 cells. Of course, the preferred cells are human when the intended patient is human. However, as OS also affects dogs, canine cells expressing the CARs herein may be used in treatment of OS in dogs.

The pharmaceutical compositions herein can be any composition suitable for administration of therapeutic cells to a patient. The most common administration route for CAR T cells is intravenous administration. Accordingly, said pharmaceutical compositions may for example be sterile aqueous solutions with a neutral pH. For example, a patient's peripheral blood mononuclear cells may be obtained via a standard leukapheresis procedure. The mononuclear cells may be enriched for T cells, before transducing them with a lentiviral vector or mRNA encoding the CARs. Said cells may then be activated with anti-CD3/CD28 antibody coated beads. The transduced T cells may be expanded in cell culture, washed, and formulated into a sterile suspension, which can be cryopreserved. If so, the product is thawed prior to administration.

One issue related to efficient access of CAR T cells at the target site of osteosarcoma, is to circumvent defenses from solid tumors. In contrast to hematological malignancies, recognition of solid tumors requires egress from the blood into the tumor site, and many malignancies evolve such that T cell infiltration is actively impeded. In situations where the tumor is localized, different administrations methods may be used to improve efficacy. For example, regional rather than systemic administration of CAR T cells might enhance efficacy.

The pharmaceutical compositions may comprise a pharmaceutically effective dose of the immune cells herein. A pharmaceutically effective dose may for example be in the range of $1\times10^6$ to $1\times10^9$ immune cells expressing the CARs. A pharmaceutically effective dose may for example be in the range of $1\times10^7$ to $5\times10^8$ T cells expressing the CARs.

For efficient expression of the claimed CARs in immune cells, a conventional leader peptide (i.e. signal peptide or L-chain) may be introduced N-terminally for facilitating location in the cell membrane. The leader peptide is believed to be trimmed off and will likely not be present in the functional CAR in the cell membrane. It is found that the nucleic acids encoding the CARs herein is successfully transcribed and the CARs are successfully translocated to the cell membrane when the leader peptide is represented by SEQ ID NO 10. This is visualized in FIG. 1. The nucleic acids encoding the claimed CARs can be in the form of well-known RNA e.g. mRNA or DNA expression vectors e.g. retroviral vectors. However, it is found that a CAR comprising a TP3 scFv (e.g. OSCAR3) was better expressed than an otherwise identical CAR comprising a TP1 scFv (e.g. OSCAR1) in T cells transduced with mRNA encoding them. Accordingly, CARs comprising a TP3 scFv would be preferred for transient expression in immune cells via mRNA transduction. In particular, mRNA encoding OSCAR3 may be preferred for transient expression in T cells. Transient expression of CARs via mRNA transduction has safety advantages compared to retroviral CAR expression systems.

It is also found that CARs comprising a TP1 scFv (e.g. OSCAR1) provided an improved long-term survival in the aggressive metastatic OS model. Accordingly, CARs comprising a TP1 scFv could be preferred for retroviral expression in immune cells. In particular, retroviral vectors encoding OSCAR1 may be preferred for long-term expression in T cells.

In one embodiment, the nucleic acids encode L-chain-VL-Linker-VH-CD8α hinge domain-CD8α transmembrane domain-4-1BB costimulatory domain-CD3ζ signaling domain. In one embodiment, the nucleic acids encode L-chain-VH-Linker-VL-CD8α hinge domain-CD8α transmembrane domain-4-1BB costimulatory domain-CD3ζ signaling domain. In one embodiment, a pharmaceutical composition is provided which comprises a pharmaceutically effective dose of T cells or NK cells expressing a CAR wherein the antigen binding domain is a TP1scFv-fragment, as described herein, for use in treatment of osteosarcoma. In one embodiment, the TP1 scFv-fragment comprises a TP1 VL and a TP1 VH connected by a peptide linker.

In one particular embodiment, a pharmaceutical composition is provided which comprises a pharmaceutically effective dose of T cells or NK cells expressing a CAR wherein the antigen binding domain comprises SEQ ID NO 1 and SEQ ID NO 2, and wherein said CAR comprises a CD8α hinge domain, a CD8α transmembrane domain, and wherein the intracellular signaling domain comprises a 4-1BB costimulatory domain and a CD3ζ signaling domain, for use in treatment of osteosarcoma.

In one embodiment, a pharmaceutical composition is provided which comprises a pharmaceutically effective dose of T cells or NK cells expressing a CAR wherein the antigen binding domain is a TP3 scFv-fragment, as described herein, for use in treatment of osteosarcoma. In one embodiment, the TP3 scFv-fragment comprises a TP3 VL and a TP3 VH connected by a peptide linker.

In one particular embodiment, a pharmaceutical composition is provided which comprises a pharmaceutically effective dose of T cells or NK cells expressing a CAR wherein the antigen binding domain is a scFv comprising SEQ ID NO 3 and SEQ ID NO 4, and wherein said CAR comprises a CD8α hinge domain, a CD8α transmembrane domain, and wherein the intracellular signaling domain comprises a 4-1BB costimulatory domain and a CD3ζ signaling domain, for use in treatment of osteosarcoma.

In one embodiment, a pharmaceutical composition is provided which comprises a pharmaceutically effective dose of T cells or NK cells expressing a CAR wherein the antigen binding domain is a TP1 scFv-fragment, as described herein, for use in treatment of metastatic osteosarcoma. In one embodiment, the TP1 scFv-fragment comprises a TP1 VL and a TP1 VH connected by a peptide linker.

In one particular embodiment, a pharmaceutical composition is provided which comprises a pharmaceutically effective dose of T cells or NK cells expressing a CAR wherein the antigen binding domain is a scFv comprising SEQ ID NO 1 and SEQ ID NO 2, and wherein said CAR comprises a CD8α hinge domain, a CD8α transmembrane domain, and wherein the intracellular signaling domain comprises a 4-1BB costimulatory domain and a CD3ζ signaling domain, for use in treatment of metastatic osteosarcoma.

In one embodiment, a pharmaceutical composition is provided which comprises a pharmaceutically effective dose of T cells or NK cells expressing a CAR wherein the antigen binding domain a TP3 scFv-fragment, as described herein, for use in treatment of metastatic osteosarcoma. In one embodiment, the TP3 scFv-fragment comprises a TP3 VL and a TP3 VH connected by a peptide linker.

In one particular embodiment, a pharmaceutical composition is provided which comprises a pharmaceutically effective dose of T cells or NK cells expressing a CAR; wherein the antigen binding domain is a scFv comprising SEQ ID NO 3 and SEQ ID NO 4, and wherein said CAR comprises a CD8α hinge domain, a CD8α transmembrane domain, and wherein the intracellular signaling domain comprises a 4-1BB costimulatory domain and a CD3ζ signaling domain, for use in treatment of metastatic osteosarcoma.

In one particular embodiment, a pharmaceutical composition is provided which comprises a pharmaceutically effective dose of T cells or NK cells expressing a CAR; wherein the antigen binding domain is a scFv comprising SEQ ID NO 3 or sequences with more than 80% sequence identity thereto and SEQ ID NO 4 or sequences with more than 80% sequence identity thereto, and wherein said CAR comprises a CD8α hinge domain, a CD8α transmembrane domain, and wherein the intracellular signaling domain comprises a 4-1BB costimulatory domain and a CD3ζ signaling domain, for use in treatment of metastatic osteosarcoma.

In one embodiment, a pharmaceutical composition is provided which comprises a pharmaceutically effective dose of T cells or NK cells expressing a CAR wherein the antigen binding domain comprises a TP1 scFv-fragment, as described herein, for use in treatment of micrometastatic osteosarcoma. In one embodiment, the TP1 scFv-fragment comprises a TP1 VL and a TP1 VH connected by a peptide linker.

In one particular embodiment, a pharmaceutical composition is provided which comprises a pharmaceutically effective dose of T cells or NK cells expressing a CAR wherein the antigen binding domain is a scFv comprising SEQ ID NO 1 and SEQ ID NO 2, and wherein said CAR comprises a CD8α hinge domain, a CD8α transmembrane domain, and wherein the intracellular signaling domain comprises a 4-1BB costimulatory domain and a CD3ζ signaling domain, for use in treatment of micrometastatic osteosarcoma.

In one embodiment, a pharmaceutical composition is provided which comprises a pharmaceutically effective dose of T cells or NK cells expressing a CAR wherein the antigen binding domain comprises a TP3 scFv-fragment, as described herein, for use in treatment of micrometastatic osteosarcoma. In one embodiment, the TP3 scFv-fragment comprises a TP3 VL and a TP3 VH connected by a peptide linker.

In one particular embodiment, a pharmaceutical composition is provided which comprises a pharmaceutically effective dose of T cells or NK cells expressing a CAR; wherein the antigen binding domain is a scFv comprising SEQ ID NO 3 and SEQ ID NO 4, and wherein said CAR comprises a CD8α hinge domain, a CD8α transmembrane domain, and wherein the intracellular signaling domain comprises an 4-1BB costimulatory domain and a CD3ζ signaling domain, for use in treatment of micrometastatic osteosarcoma.

In one particular embodiment, a pharmaceutical composition is provided which comprises a pharmaceutically effective dose of human T cells or NK cells expressing a CAR wherein the antigen binding domain comprises SEQ ID NO 1 or sequences with more than 90% sequence identity to SEQ ID NO 1 provided the CDRs are unmodified; and SEQ ID NO 2 or sequences with more than 90% sequence identity to SEQ ID NO 2 provided the CDRs are unmodified, and wherein said CAR comprises a CD8α hinge domain, a CD8α transmembrane domain, and wherein the intracellular signaling domain comprises a 4-1BB costimulatory domain and a CD3ζ signaling domain, for use in treatment of metastatic osteosarcoma in a human patient.

In one particular embodiment, a pharmaceutical composition is provided which comprises a pharmaceutically effective dose of human T cells or NK cells expressing a CAR wherein the antigen binding domain comprises SEQ ID NO 3 or sequences with more than 90% sequence identity to SEQ ID NO 3 provided the CDRs are unmodified; and SEQ ID NO 4 or sequences with more than 90% sequence identity to SEQ ID NO 4 provided the CDRs are unmodified, and wherein said CAR comprises a CD8α hinge domain, a CD8α transmembrane domain, and wherein the intracellular signaling domain comprises a 4-1BB costimulatory domain and a CD3ζ signaling domain, for use in treatment of metastatic osteosarcoma in a human patient.

In one particular embodiment, a pharmaceutical composition is provided which comprises a pharmaceutically effective dose of canine T cells or NK cells expressing a CAR wherein the antigen binding domain comprises SEQ ID NO 1 or sequences with more than 90% sequence identity to SEQ ID NO 1 provided the CDRs are unmodified; and SEQ ID NO 2 or sequences with more than 90% sequence identity to SEQ ID NO 2 provided the CDRs are unmodified, and wherein said CAR comprises a CD8α hinge domain, a CD8α transmembrane domain, and wherein the intracellular signaling domain comprises a 4-1BB costimulatory domain and a CD3ζ signaling domain, for use in treatment of osteosarcoma in a dog.

In one particular embodiment, a pharmaceutical composition is provided which comprises a pharmaceutically effective dose of canine T cells or NK cells expressing a CAR wherein the antigen binding domain comprises SEQ ID NO 3 or sequences with more than 90% sequence identity to SEQ ID NO 3 provided the CDRs are unmodified; and SEQ ID NO 4 or sequences with more than 90% sequence identity to SEQ ID NO 4 provided the CDRs are unmodified, and wherein said CAR comprises a CD8α hinge domain, a CD8α transmembrane domain, and wherein the intracellular signaling domain comprises a 4-1BB costimulatory domain and a CD3ζ signaling domain, for use in treatment of osteosarcoma in a dog.

Many patients diagnosed with localized OS develop OS metastases. Metastatic OS is osteosarcoma that has spread from the initially affected bone to one or more sites in the body, distant from the site of origin. Detectable OS metastases are present in the majority of patients at the time of primary diagnosis. Despite the surgical resection of such detected lung metastases, any remaining micrometastases may cause subsequent relapses and, ultimately death. It is believed that OS micrometastases are present in the majority of patients after surgical resection of detected lung metastases. Micrometastatic tumors are mostly undetectable by current procedures due to their small size, hence the name micrometastatic OS. However, upon intravenous infusion, the CAR expressing immune cells herein may migrate to the lungs and infiltrate such micrometastatic tumors. In particular, when CAR T cells successfully bind their target in an OS micrometastatic tumor, and the T cells are successfully activated, a cytotoxic effect may be triggered. The pharmaceutical compositions disclosed herein may thus offer an alternative therapy of metastatic OS and/or micrometastatic OS.

In one particular embodiment, a method of treatment of osteosarcoma is provided, comprising the steps:
  a) transducing a population of NK cells and/or T cells with a viral vector encoding a CAR comprising a TP1 scFv-fragment,
  b) administering a pharmaceutical composition comprising the cells from step a) to a patient diagnosed with osteosarcoma.

In one particular embodiment, a method of treatment of osteosarcoma is provided, comprising the steps:
  a) transducing a population of NK cells and/or T cells with a viral vector encoding OSCAR1,
  b) intravenously administering a pharmaceutical composition comprising the cells from step a) to a patient diagnosed with osteosarcoma.

In one particular embodiment, a method of treatment of metastatic osteosarcoma is provided, comprising the steps:
a) transducing a population of NK cells and/or T cells with a viral vector encoding OSCAR1,
b) intravenously administering a pharmaceutical composition comprising the cells from step a) to a patient diagnosed with metastatic osteosarcoma.

In one particular embodiment, a method of treatment of micrometastatic osteosarcoma is provided, comprising the steps:
a) transducing a population of NK cells and/or T cells with a viral vector encoding OSCAR1,
b) administering a pharmaceutical composition comprising the cells from step a) to a patient previously diagnosed with metastatic osteosarcoma, wherein no detectable metastasis is currently detected.

In one particular embodiment, a method of treatment of osteosarcoma is provided, comprising the steps:
a) transducing a population of NK cells and/or T cells with mRNA encoding a CAR comprising a TP3 scFv-fragment,
b) administering a pharmaceutical composition comprising the cells from step a) to a patient diagnosed with osteosarcoma.

In one particular embodiment, a method of treatment of osteosarcoma is provided, comprising the steps:
a) transducing a population of NK cells and/or T cells with mRNA encoding OSCAR3,
b) administering a pharmaceutical composition comprising the cells from step a) to a patient diagnosed with osteosarcoma.

In one particular embodiment, a method of treatment of metastatic osteosarcoma is provided, comprising the steps:
a) transducing a population of NK cells and/or T cells with mRNA encoding OSCAR3,
b) administering a pharmaceutical composition comprising the cells from step a) to a patient diagnosed with metastatic osteosarcoma.

In one particular embodiment, a method of treatment of micrometastatic osteosarcoma is provided, comprising the steps:
a) transducing a population of NK cells and/or T cells with mRNA encoding OSCAR3,
b) administering a pharmaceutical composition comprising the cells from step a) to a patient previously diagnosed with metastatic osteosarcoma, wherein no detectable metastasis is currently detected.

```
Sequences:

SEQ ID NO 1 (TP1 VL with CDRs boxed)
DIVMTQSHKFMSTSVGDRVSITCKASQGVGSAIAWYQQKTGQSPKLLIYWASIRHTGVPDRFTGSGSG

TDFTLTISNVQSEDLADYFCQQYSNYPLTFGGGTKLEIKR

SEQ ID NO 2 (TP1 VH with CDRs boxed)
EVQLQESGPSLVKPSQTLSLTCSVTGDSITSGYWNWIRKFPGNKLEYMGYISYSDTTYYNPSLKSRIS

ITRDTSKNQYYLHLKSVTTEDTATYYCASAYYGSSLSMGNWGQGTSATVSS

SEQ ID NO 3 (TP3 VL with CDRs boxed)
DIVLTQSPASLAVSLGQRATISCRASKSVSTGYSYLHWYQQKPGQPPKLLIYLASNLESGVPARFSGS

GSGTDFTLNIHPVEEEDAATYYCQHSRELPLTFGAGTKLELKR

SEQ ID NO 4 (TP3 VH with CDRs boxed)
EVQLQQSGAELVKPGASVKISCKASGYTFTDYNMDWVKQSHGKSLEWIGDINPNYDSTRYNQKFKGKA

TLTVDKSSSTAYMELRSLTSEDTAVYYCARGDYYVSSYGHDYAMDYWGQGTSVTVSS

SEQ ID NO 5 CD8α hinge domain
FVPVFLPAKPTTTPAPRPPTPAPTIASQPLSLRPEACRPAAGGAVHTRGLDFACD SEQ ID NO 6 CD8α transmembrane domain
IYIWAPLAGTCGVLLLSLVIT SEQ ID NO 7 4-1BB costimulatory domain
RFSVVKRGRKKLLYIFKQPFMRPVQTTQEEDGCSCRFPEEEEGGCEL SEQ ID NO 8 CD3ζ signaling domain
RVKFSRSADAPAYQQGQNQLYNELNLGRREEYDVLDKRRGRDPEMGGKPQRRKNPQEGLYNELQKDKM
AEAYSEIGMKGERRRGKGHDGLYQGLSTATKDTYDALHMQALPPR SEQ ID NO 9 Linker
GGGGSGGGGSGGGGSGGGGS SEQ ID NO 10 L-chain
METDTLLLWVLLLWVPGSTG
```

EXAMPLES

Example 1

CAR Design

Two novel second-generation CARs were cloned into pENTR vector (Invitrogen) and further subcloned by recombination into Gateway system compatible expression vectors, the retroviral construct pMP71 and the mRNA synthesis construct pCIpA102 following our previous publication (Wälchli et al, PLoS One. 2011; 6(11): e27930 and Inderberg E. M., Wälchli S. (2019) Chimeric Antigen Receptor preparation from hybridoma to T-cell expression. Antibody Therapeutics, Volume 2, Issue 2, April 2019, Pages 56-63).

The CAR sequence encoded by the vectors was L-chain-VL-chain-Linker-VH-chain-CD8α hinge domain-CD8α transmembrane domain-4-1BB costimulatory domain-CD3ζ signaling domain.

Accordingly, the vector for expressing OSCAR1, encoded SEQ ID NO 10-SEQ ID NO 1-SEQ ID NO 9-SEQ ID NO 2-SEQ ID NO 5-SEQ ID NO 6-SEQ ID NO 7-SEQ ID NO 8.

The vector for expressing OSCAR3, encoded SEQ ID NO 10-SEQ ID NO 3-SEQ ID NO 9-SEQ ID NO 4-SEQ ID NO 5-SEQ ID NO 6-SEQ ID NO 7-SEQ ID NO 8.

Example 2

CAR Expression

Retroviral particles of the OSCAR1 and OSCAR3 from Example 1 were prepared and primary T cells isolated from healthy donors peripheral blood mononuclear cells (PBMC) were transduced by well known methods (Wälchli et al, PLoS One. 2011; 6(11):e27930). After 48 hours, the presence of the CAR was analyzed by flow cytometry using an anti-mouse Fab antibody (anti-CAR). The result is included in FIG. 1.

In the following examples, T cells expressing OSCAR1 or OSCAR3 are compared to untransduced T cells (mock). T cells are in some figures abbreviated Tc.

Accordingly, both "OSCAR1 Tc" and "Tc OSCAR-1" means T cells expressing OSCAR1. Accordingly, both "OSCAR3 Tc" and "Tc OSCAR-3" means T cells expressing OSCAR3.

Example 3

CAR Function In Vitro (Killing and Cytokine Release)

T cell alone (mock), T cells expressing OSCAR1 and T cells expressing OSCAR3 were incubated for 24 hours with the indicated target cells. The supernatant was then harvested, and cytokine presence was detected by BioPlex. As shown, the OSCAR redirected cells were strongly activated for TNFα and IFNγ release upon specific stimulation.

Figure 3A:
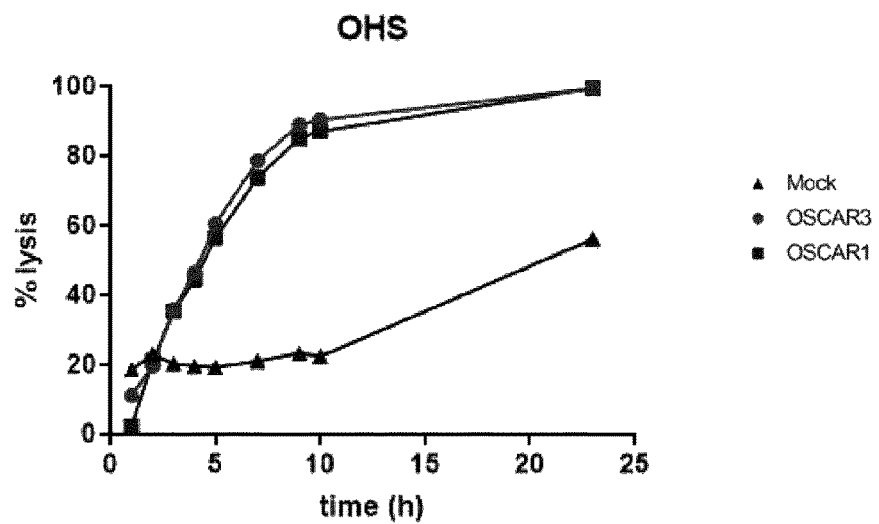
FIG. 3a displays in vitro killing (BLI-assay) of OHS cells by primary T cells expressing either OSCAR1 or OSCAR3 or mock transfected.
Figure 3B:
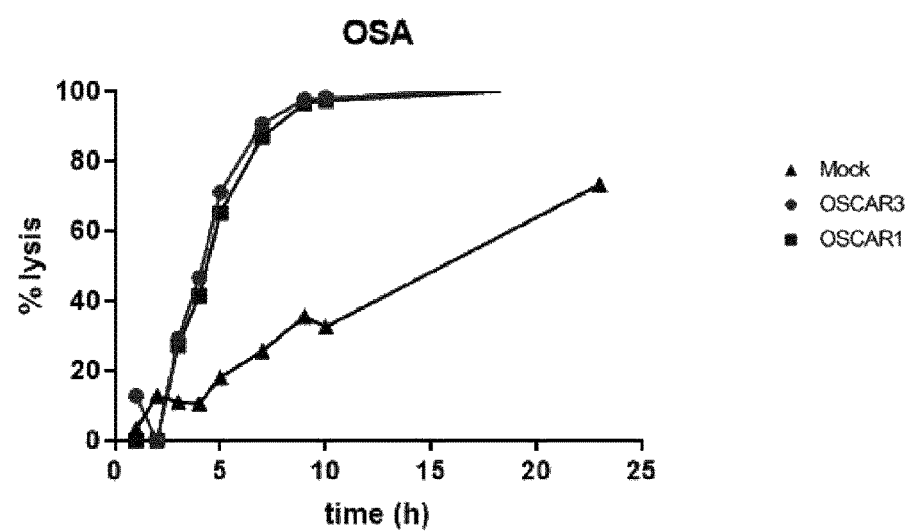
FIG. 3b displays in vitro killing (BLI-assay) of OSA cells by primary T cells expressing either OSCAR1 or OSCAR3 or mock transfected.
Figure 3C:
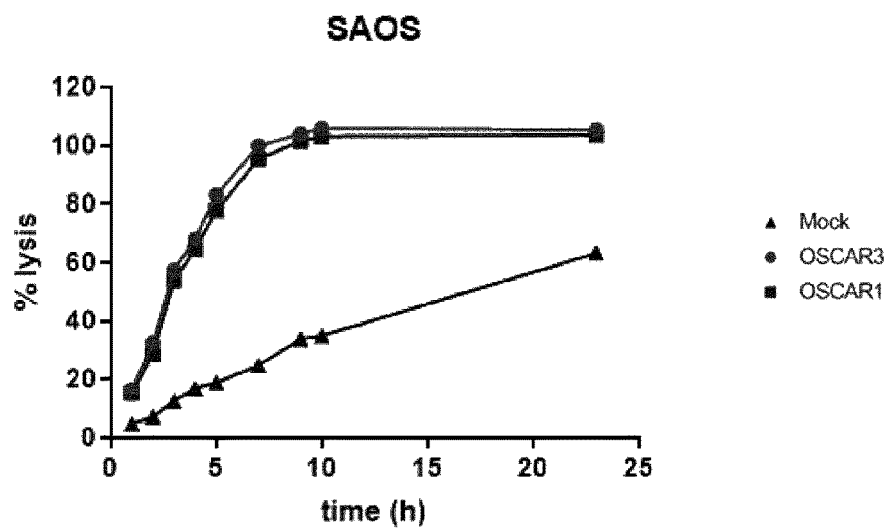
FIG. 3c displays in vitro killing (BLI-assay) of SAOS cells by primary T cells expressing either OSCAR1 or OSCAR3 or mock transfected.

In Vitro Killing of Target Cell Lines:

In vitro killing of target cell lines was demonstrated by incubating T cells expressing OSCAR1 or OSCAR3 with osteosarcoma cell lines (OHS, SAOS-2, OSA) for 20 hours. All the target cells constitutively expressed the luciferase gene fused to GFP, the presence of luciferase is used to detect cell killing upon addition of luciferase substrate by a known method (Walseng et al, Sci Rep. 2017 Sep. 6; 7(1):10713). T cell killing was monitored by measuring the variation in luciferase signal in the target cells (BLI assay). The results are shown in FIGS. 3a, 3b and 3c.

Example 4

CAR Function In Vivo (Xenograft Models)

In order to assess CAR efficacy, an animal model was used in which human osteosarcoma cell lines were engrafted in mice. The engraftment was performed by intra-peritoneal injection of $10^6$ OHS cells expressing the luciferase gene. When the tumor became palpable, the mice were randomized and treated or not with T cells redirected or not with OSCAR1 or OSCAR3. Three injections of $10 \times 10^6$ T cells were performed and the tumor growth was monitored by IVIS (luciferase signal detection). In addition, the mice survival was also studied. Conditions: 5 mice per group, N=2.

Figure 4A:
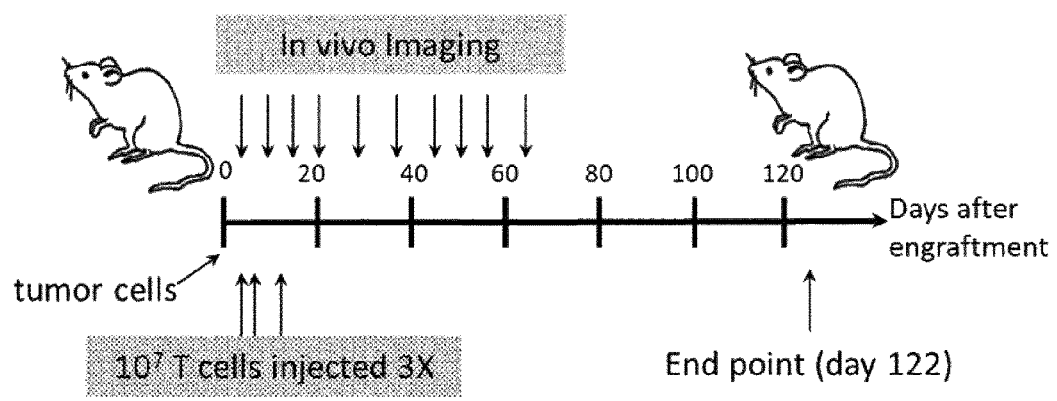
FIG. 4a depicts the treatment protocol for the intraperitoneal mouse model as described in Example 4
Figure 4B:
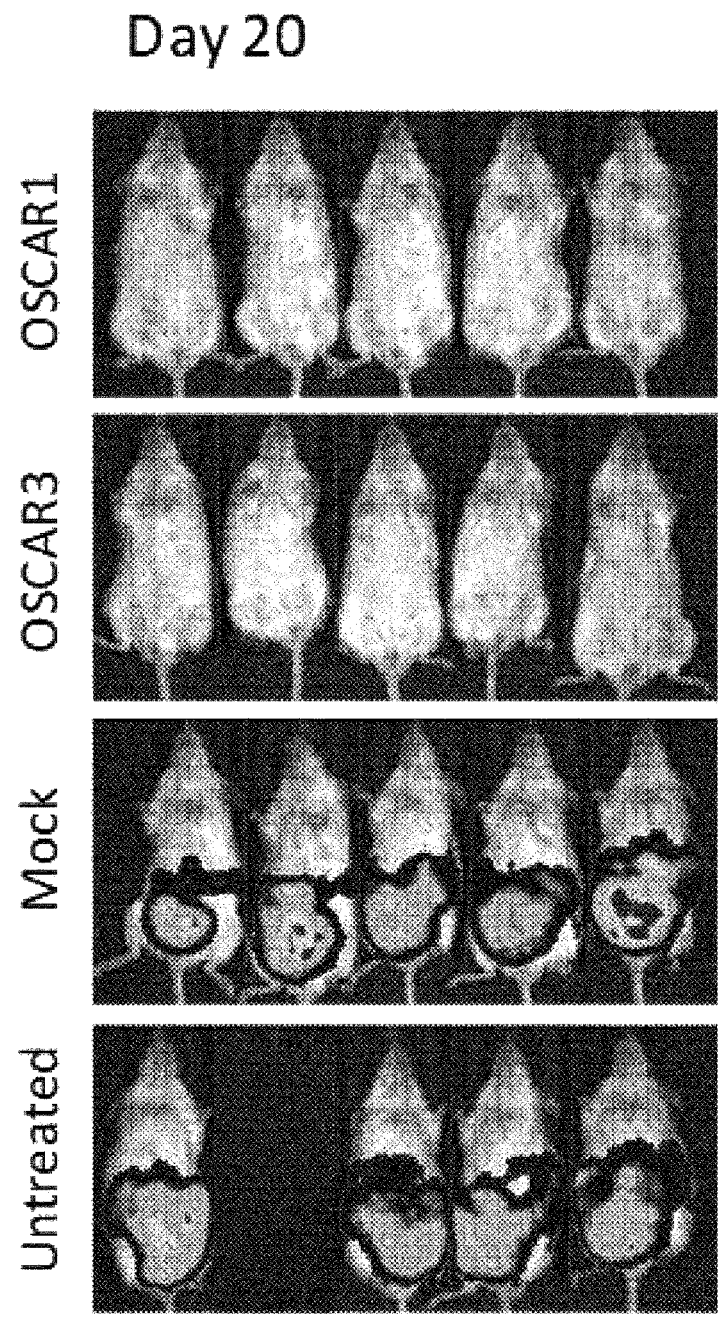
FIG. 4b depicts the OHS tumor burden (luciferase signal detection detected by IVIS) and survival on day 20 of the mice treated as described in Example 4.
Figure 4C:
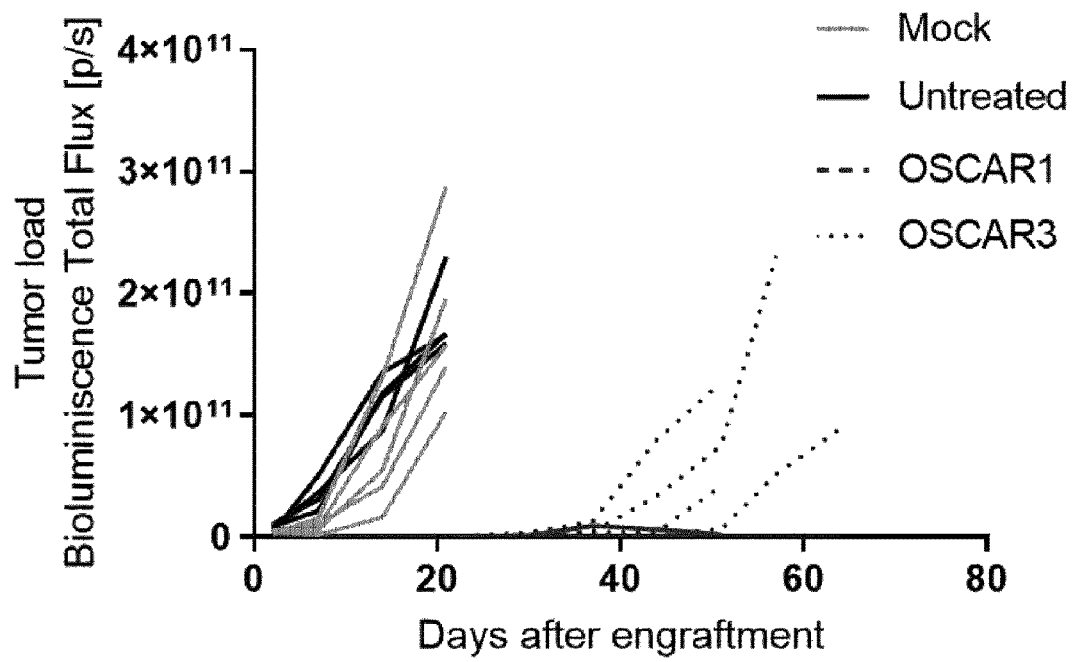
FIG. 4c is a spider plot of the luciferase signal for each mouse treated as described in Example 4. OSCAR1 and OSCAR3 could control tumor growth in most of the animals whereas tumor relapse was observed for the OSCAR3 treated animals compared with animals treated with mock T cell (control).
Figure 4D:
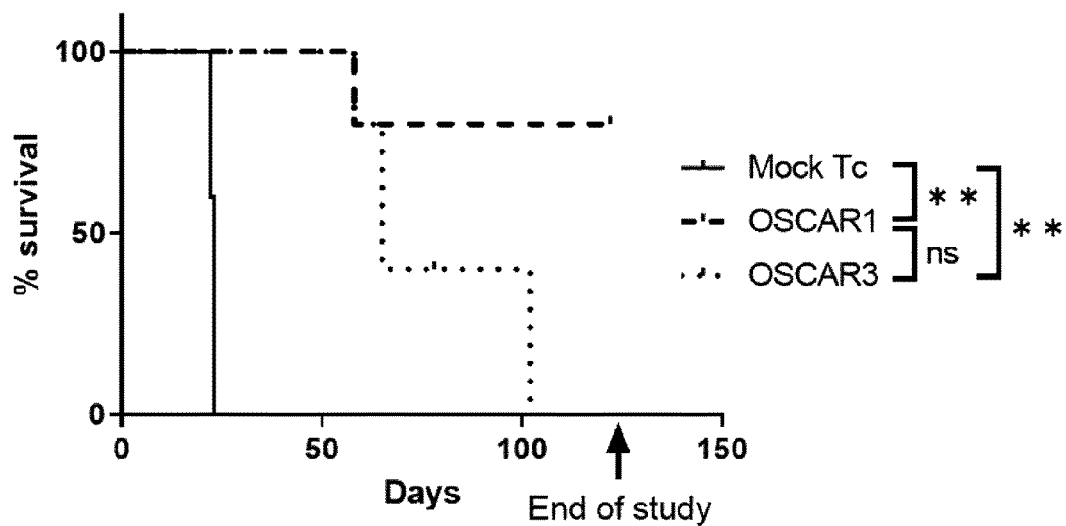
FIG. 4d is a survival curve (Kaplan-Meier) of mice treated as described in Example 4. T cells expressing OSCAR1 kept 80% of the mice alive at the end point. T cells expressing OSCAR3 performed better than mock and saline treated animals.

FIG. 4a depicts the protocol and the time line of the treatment. FIG. 4b is an example of IVIS picture (here Day 20) of the mice treated as indicated on the left. As shown, OSCAR1 and OSCAR3 treated animals showed very low to undetectable tumor burden at day 20. FIG. 4c is a spider plot of the luciferase signal for each animal, showing that OSCAR constructs could control the tumor development. This was in line with the survival curve (Kaplan-Meier) in FIG. 4d, which shows that 80% of the OSCAR1 treated animals were alive at the end point. OSCAR3 treated animals performed better than mock and saline treated animals and were not statistically different to OSCAR1 animals on the survival curve.

Example 5

CAR Function In Vivo (Xenograft Models)

Figure 5A:
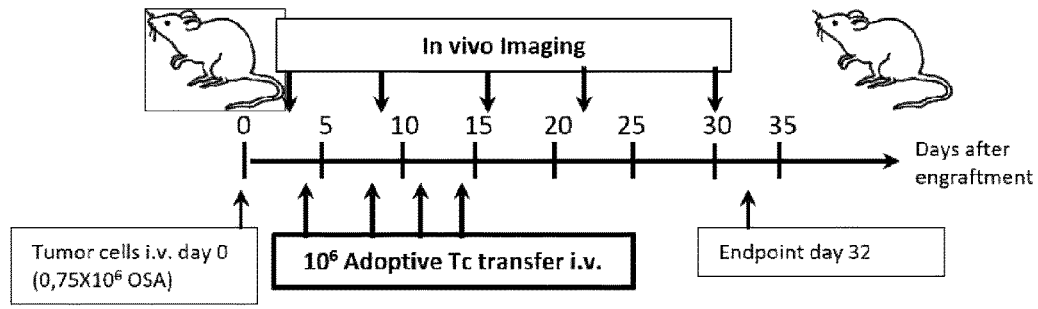
FIG. 5a depicts the treatment protocol for a lung metastasis tumor model as described in Example 5.
Figure 5B:
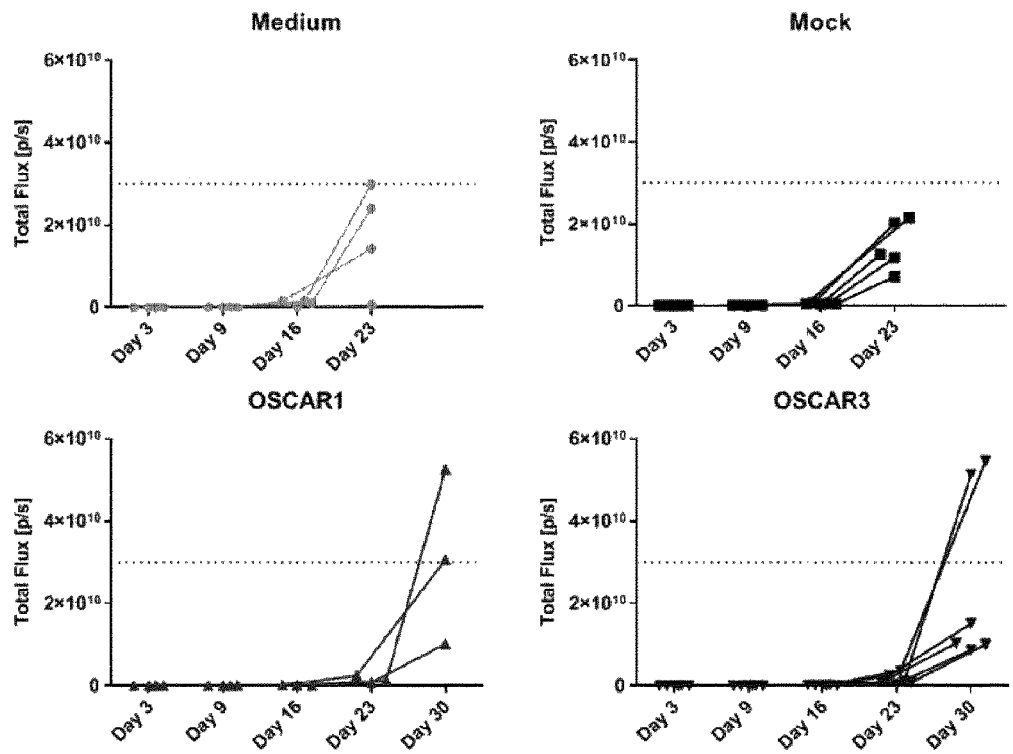
FIG. 5b depicts tumor progression in mice treated as described in Example 5. As shown, the OSA tumor growth was controlled for a longer time by T cells expressing OSCAR1 or OSCAR3 compared to mock or medium treated animals.

We also used a lung metastasis tumor model where nod-scid mice were intravenously (iv) injected with OSA (luciferase+) cell line as depicted in FIG. 5a. This cell line colonized the lungs and established aggressive tumors that lead to animal death after ca 25-30 days. After 4 days, the tumor burden was detectable in the lungs and the mice were randomized and treated with OSCAR T cells. Mice were iv injected four times with $10^6$ OSCAR-redirected T cells and tumor progression was analyzed by IVIS. As shown, the tumor growth was controlled for a longer time by OSCAR1 and OSCAR3 compared to mock or medium treated animals, but the animals eventually developed a tumor. Kaplan Meier curve statistically confirms this protective effect, although in this aggressive model, the animals could not be rescued.

Example 6

CAR Safety

CAR therapy can be considered as a dangerous therapy. This is mainly due to the unpredictable targeting a given construct can have against healthy tissues. In order to test the specificity of OSCAR1 and OSCAR3, a series of tests against haematopoietic cells were undertaken. The assay consists in the isolation of bone marrow from a donor as a source of stem cells. The blood from the same donor is taken and T cells are isolated and modified with the CAR of interest before being co-incubated with the stem cells. Colonies are then left to grow in different medium to expand each type of blood progenitors. When the colonies become visible, they are counted and compared to controls.

Figure 6A:
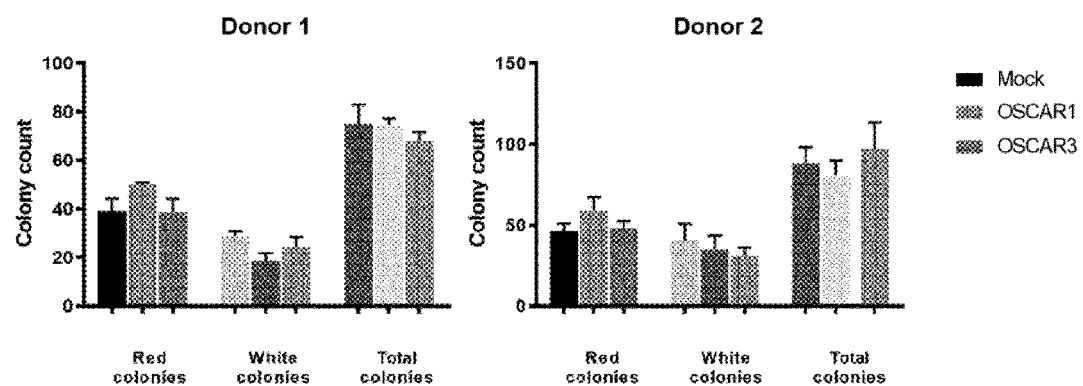
FIG. 6a demonstrates that neither T cells transiently expressing OSCAR1 nor OSCAR3 had any significant effect on the colony formation of progenitor blood cells.
Figure 6B:
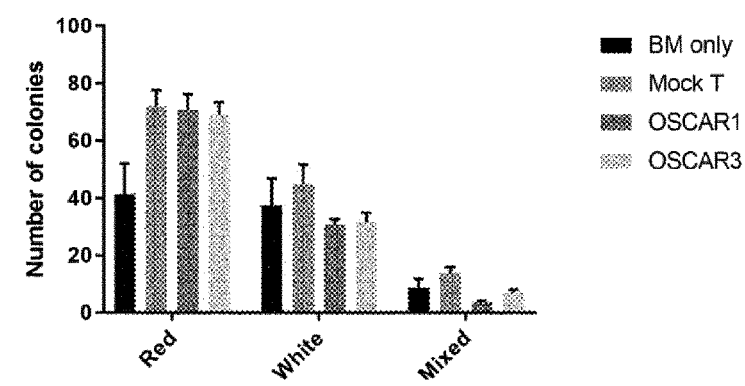
FIG. 6b demonstrates that neither T cells stably expressing OSCAR1 nor OSCAR3 had any significant effect on the colony formation of progenitor blood cells. Colony-forming unit (CFU)-erythrocyte (E) red, CFU-Granulocyte macrophages (GM) white colonies, CFU Granulocyte, erythrocyte, monocyte, megakaryocyte (GEMM) mixed colonies.

T cells from two donors were electroporated with mRNA of the indicated CAR constructs or mock electroporated. As shown in FIG. 6a, neither OSCAR1 nor OSCAR3 had any effect on the colony formation suggesting that their target is not present on preogenitor blood cells. We confirmed these data when using autologous T cells stably expressing OSCAR1 or OSCAR3, here again no statistical effect was detected (see FIG. 6b), suggesting that OSCAR did not kill hematopoietic stem cells.

Example 7

Figure 7:
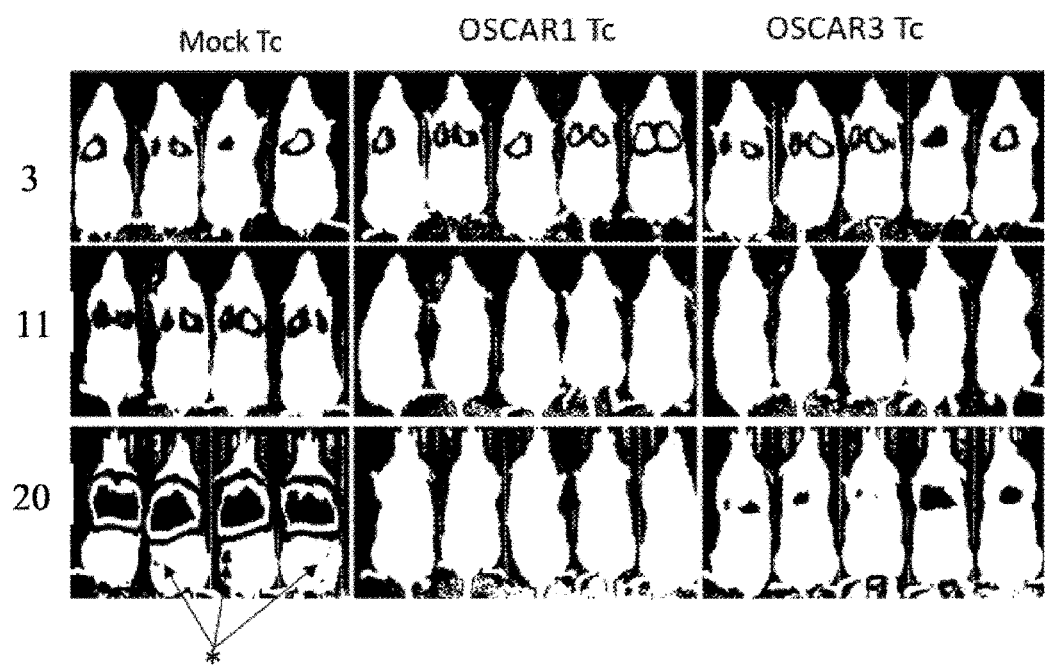
FIG. 7 demonstrates therapeutic effect T cells expressing either OSCAR1 or OSCAR3 in a second experiment using OSA cell to simulate lung metastases. The pictures are taken at 3, 11 and 20 days. Here, bone metastases (*) could be detected in the control animals.

Same experiment as Example 5 where pictures are shown (see FIG. 7) and demonstrates the presence of bone metastasis in control animals (*), whereas OSCAR treated animals controlled tumor development.

Example 8

Figure 8:
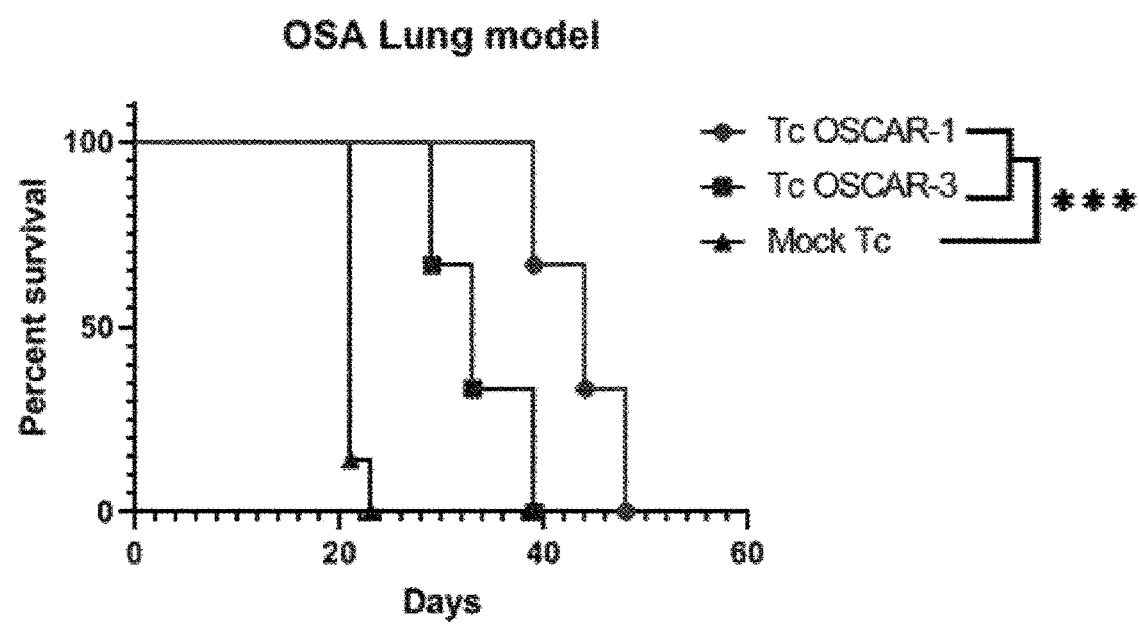
FIG. 8 is the Kaplan-Meier curve from Example 7.

Kaplan-Meier survival curve based on Example 7 demonstrating that both OSCAR1 and OSCAR3 are able to control tumor growth in the lungs, hence prolong animal survival (see FIG. 8). Note that OSA is a very aggressive cell line (Lauvrak et al. Br J Cancer. 2013 Oct. 15; 109(8): 2228-2236), and this experiment may be the first to demonstrate efficacy of CAR T cells in such a model.

Example 9

Figure 9:
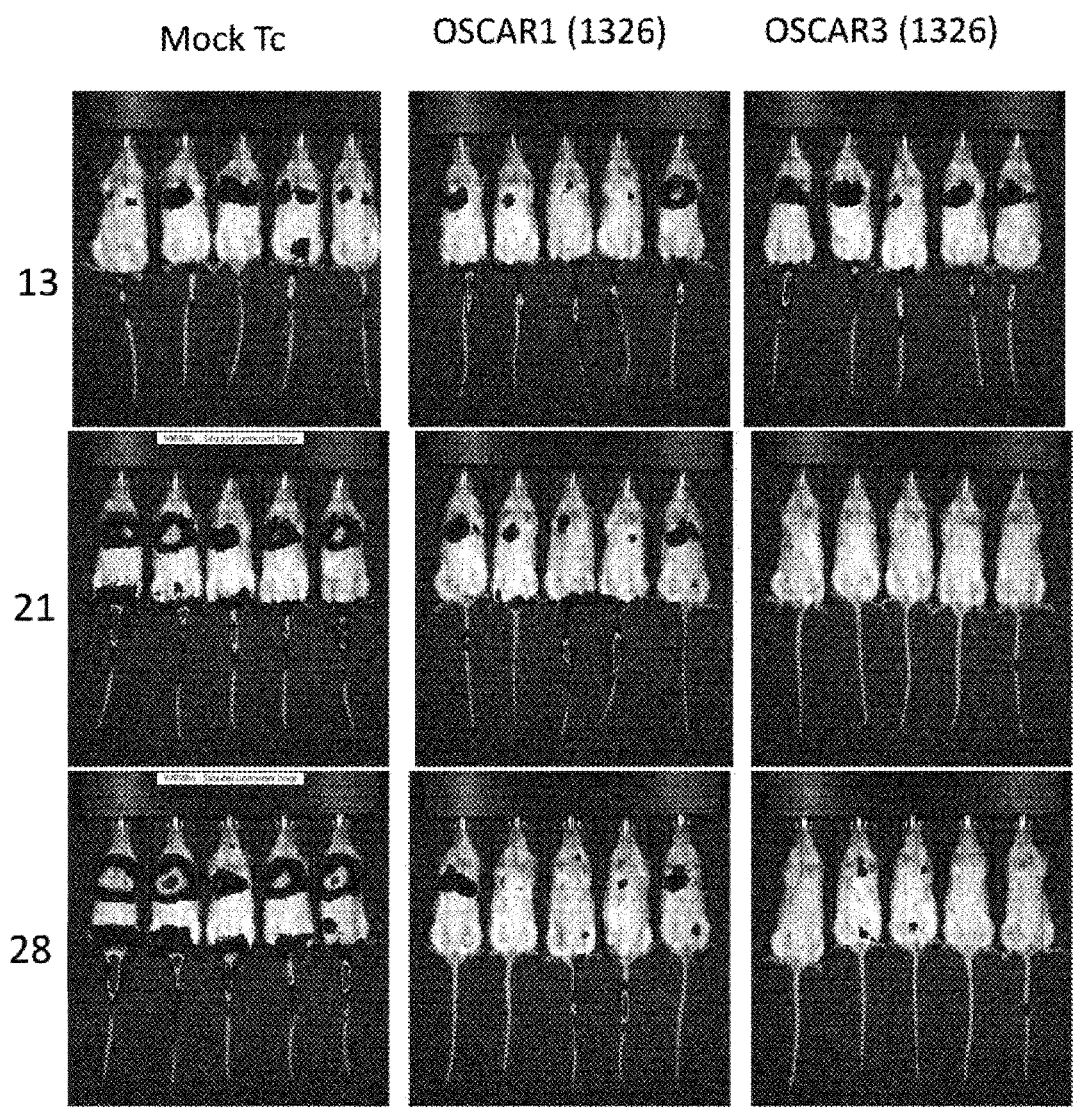
FIG. 9 In vivo experiment of another lung metastasis model using LM-7 cell line. Pictures are taken at 13, 21 and 28 days.

We used an alternative and less aggressive lung metastasis tumor model. Nod-scid mice were intravenously (iv) injected with LM-7 (luciferase+) cell line which is also recognized by OSCAR1 and OSCAR3 in vitro and forms lung metastases slower than OSA. After iv injection, this cell line colonized the lungs and established aggressive tumors that lead to animal death after ca 40-50 days. Mice were randomized 5 days after treatment and treated with OSCAR T cells. Mice were iv injected four times with $10^6$ OSCAR-redirected T cells and tumor progression was analyzed by IVIS. As shown in FIG. 9, the tumor growth was controlled by OSCARs compared to mock supporting a good efficacy of the transduced cells.

Example 10

Figure 10:
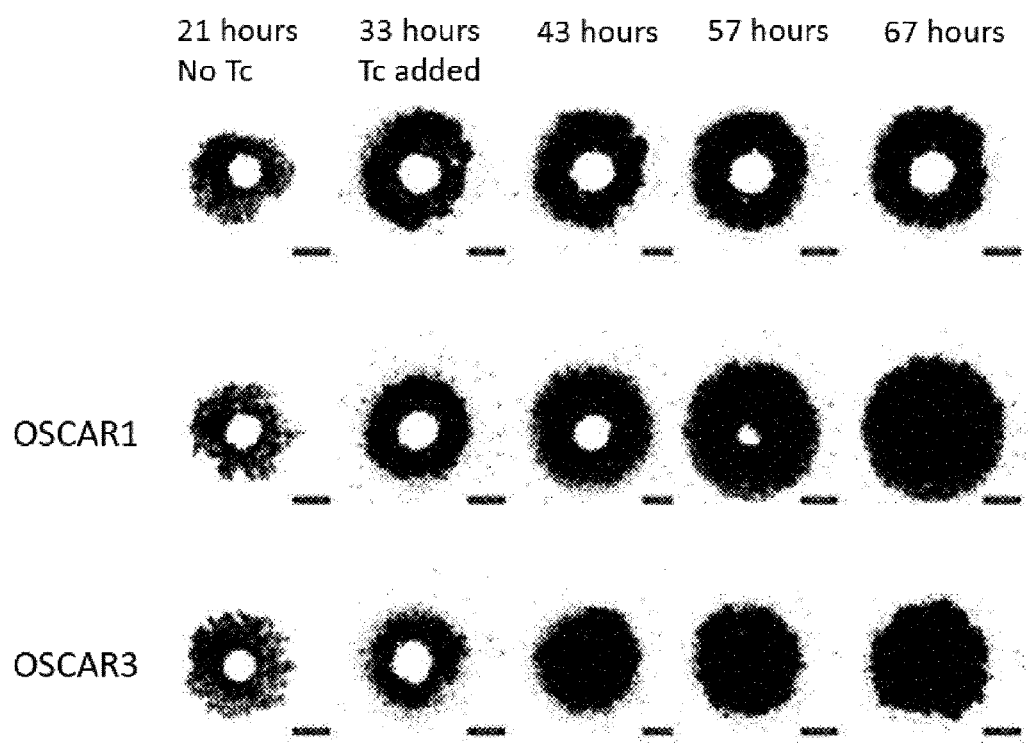
FIG. 10 demonstrates a cytotoxic effect of T cells expressing either OSCAR1 or OSCAR3 in spheroids wherein the white spot in the middle represents tumor cells (OHS cell line). The top row represents the effect of untransduced T cells (mock).

Five thousand Osteosarcoma cell (OHS cell line) derived tumor spheroids were grown for 7 days and monitored by fluorescent live cell microscopy (GFP=white). T cells (mock or OSCAR expressing) were added and pictures were taken at regular timepoints to analyze GFP signal. As shown in FIG. 10, T cells expressing either OSCAR1 or OSCAR3 are able to kill the tumor cells inside the spheroids.

The invention claimed is:

1. A Chimeric Antigen Receptor (CAR) comprising an antigen binding domain, a CD8α hinge domain, a CD8α transmembrane domain and an intracellular signaling domain; wherein
the antigen binding domain comprises a TP1 scFV-fragment comprising SEQ ID NO: 1 and SEQ ID NO: 2 connected by a peptide linker, and
the intracellular signaling domain comprises a CD3ζ signaling domain and a 4-1BB costimulatory domain.

2. The CAR according to claim 1, wherein the hinge domain is represented by SEQ ID NO: 5.

3. The CAR according to claim 1, wherein the transmembrane domain is represented by SEQ ID NO: 6.

4. The CAR according to claim 1, wherein the intracellular signaling domain consists of a CD3ζ signaling domain and a 4-1BB costimulatory domain.

5. The CAR according to claim 1, wherein the hinge domain is represented by SEQ ID NO: 5, and the transmembrane domain is represented by SEQ ID NO: 6.

6. A nucleic acid encoding the CAR according to claim 1.

7. An immune cell transduced with the nucleic acid according to claim 6.

8. An immune cell expressing the CAR according to claim 1.

9. A pharmaceutical composition comprising immune cells according to claim 7, wherein the immune cells are T cells or NK cells, wherein the pharmaceutical composition is a sterile aqueous solution.

10. A method of treating osteosarcoma comprising administering to a subject in need thereof a pharmaceutical composition according to claim 9, wherein the immune cells express the encoded CAR.

11. A method of treating metastatic osteosarcoma comprising administering to a subject in need thereof a pharmaceutical composition according to claim 9, wherein the immune cells express the encoded CAR.

12. A method of treating micrometastatic osteosarcoma comprising administering to a subject in need thereof a pharmaceutical composition according to claim 9, wherein the immune cells express the encoded CAR.

13. A method of treatment of metastatic osteosarcoma, comprising the steps:
a) transducing a population of NK cells and/or T cells with a nucleic acid as defined in claim 6, wherein the transduced cells express the encoded CAR, and
b) intravenously administering a pharmaceutical composition comprising a pharmaceutically effective dose of the cells from step a) to a patient diagnosed with metastatic osteosarcoma.

14. A pharmaceutical composition comprising immune cells according to claim 8, wherein the immune cells are T cells or NK cells, and wherein the pharmaceutical composition is a sterile aqueous solution.

* * * * *

```
SEQUENCE LISTING

<160> NUMBER OF SEQ ID NOS: 10

<210> SEQ ID NO 1
<211> LENGTH: 108
<212> TYPE: PRT
<213> ORGANISM: Homo sapiens

<400> SEQUENCE: 1

Asp Ile Val Met Thr Gln Ser His Lys Phe Met Ser Thr Ser Val Gly
1               5                   10                  15

Asp Arg Val Ser Ile Thr Cys Lys Ala Ser Gln Gly Val Gly Ser Ala
            20                  25                  30

Ile Ala Trp Tyr Gln Gln Lys Thr Gly Gln Ser Pro Lys Leu Leu Ile
        35                  40                  45

Tyr Trp Ala Ser Ile Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Asn Tyr Pro Leu
                85                  90                  95

Thr Phe Gly Gly Gly Thr Lys Leu Glu Ile Lys Arg
            100                 105

<210> SEQ ID NO 2
<211> LENGTH: 119
<212> TYPE: PRT
<213> ORGANISM: Homo sapiens

<400> SEQUENCE: 2

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Asp Thr Thr Tyr Tyr Asn Pro Ser Leu Lys
```

```
                50                  55                  60
Ser Arg Ile Ser Ile Thr Arg Asp Thr Ser Lys Asn Gln Tyr Tyr Leu
 65                  70                  75                  80

His Leu Lys Ser Val Thr Thr Glu Asp Thr Ala Thr Tyr Tyr Cys Ala
                 85                  90                  95

Ser Ala Tyr Tyr Gly Ser Ser Leu Ser Met Gly Asn Trp Gly Gln Gly
                100                 105                 110

Thr Ser Ala Thr Val Ser Ser
            115
```

<210> SEQ ID NO 3
<211> LENGTH: 111
<212> TYPE: PRT
<213> ORGANISM: Homo sapiens

<400> SEQUENCE: 3

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Gly
                 20                  25                  30

Tyr Ser Tyr Leu His Trp Tyr Gln Gln Lys Pro Gly Gln Pro Pro Lys
             35                  40                  45

Leu Leu Ile Tyr Leu Ala Ser Asn Leu Glu Ser Gly Val Pro Ala Arg
 50                  55                  60

Phe Ser Gly Ser Gly Ser Gly Thr Asp Phe Thr Leu Asn Ile His Pro
 65                  70                  75                  80

Val Glu Glu Glu Asp Ala Ala Thr Tyr Tyr Cys Gln His Ser Arg Glu
                 85                  90                  95

Leu Pro Leu Thr Phe Gly Ala Gly Thr Lys Leu Glu Leu Lys Arg
                100                 105                 110
```

<210> SEQ ID NO 4
<211> LENGTH: 125
<212> TYPE: PRT
<213> ORGANISM: Homo sapiens

<400> SEQUENCE: 4

```
Glu Val Gln Leu Gln Gln Ser Gly Ala Glu Leu Val Lys Pro Gly Ala
 1               5                  10                  15

Ser Val Lys Ile Ser Cys Lys Ala Ser Gly Tyr Thr Phe Thr Asp Tyr
                 20                  25                  30

Asn Met Asp Trp Val Lys Gln Ser His Gly Lys Ser Leu Glu Trp Ile
             35                  40                  45

Gly Asp Ile Asn Pro Asn Tyr Asp Ser Thr Arg Tyr Asn Gln Lys Phe
 50                  55                  60

Lys Gly Lys Ala Thr Leu Thr Val Asp Lys Ser Ser Ser Thr Ala Tyr
 65                  70                  75                  80

Met Glu Leu Arg Ser Leu Thr Ser Glu Asp Thr Ala Val Tyr Tyr Cys
                 85                  90                  95

Ala Arg Gly Asp Tyr Tyr Val Ser Ser Tyr Gly His Asp Tyr Ala Met
                100                 105                 110

Asp Tyr Trp Gly Gln Gly Thr Ser Val Thr Val Ser Ser
            115                 120                 125
```

<210> SEQ ID NO 5
<211> LENGTH: 55
<212> TYPE: PRT

<213> ORGANISM: Homo sapiens

<400> SEQUENCE: 5

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
                20                  25                  30

Arg Pro Glu Ala Cys Arg Pro Ala Ala Gly Gly Ala Val His Thr Arg
            35                  40                  45

Gly Leu Asp Phe Ala Cys Asp
        50                  55

<210> SEQ ID NO 6
<211> LENGTH: 21
<212> TYPE: PRT
<213> ORGANISM: Homo sapiens

<400> SEQUENCE: 6

Ile Tyr Ile Trp Ala Pro Leu Ala Gly Thr Cys Gly Val Leu Leu Leu
1               5                   10                  15

Ser Leu Val Ile Thr
            20

<210> SEQ ID NO 7
<211> LENGTH: 47
<212> TYPE: PRT
<213> ORGANISM: Homo sapiens

<400> SEQUENCE: 7

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
                20                  25                  30

Cys Ser Cys Arg Phe Pro Glu Glu Glu Gly Gly Cys Glu Leu
            35                  40                  45

<210> SEQ ID NO 8
<211> LENGTH: 113
<212> TYPE: PRT
<213> ORGANISM: Homo sapiens

<400> SEQUENCE: 8

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

```
<210> SEQ ID NO 9
<211> LENGTH: 20
<212> TYPE: PRT
<213> ORGANISM: Artificial Sequence
<220> FEATURE:
<223> OTHER INFORMATION: Linker

<400> SEQUENCE: 9

Gly Gly Gly Gly Ser Gly Gly Gly Gly Ser Gly Gly Gly Gly Ser Gly
1               5                   10                  15

Gly Gly Gly Ser
            20

<210> SEQ ID NO 10
<211> LENGTH: 20
<212> TYPE: PRT
<213> ORGANISM: Artificial Sequence
<220> FEATURE:
<223> OTHER INFORMATION: L-chain

<400> SEQUENCE: 10

Met Glu Thr Asp Thr Leu Leu Leu Trp Val Leu Leu Leu Trp Val Pro
1               5                   10                  15

Gly Ser Thr Gly
            20
```